United States Patent [19]
Toda et al.

[11] Patent Number: 5,433,253
[45] Date of Patent: Jul. 18, 1995

[54] CLOTH ABNORMALITY INSPECTING DEVICE WITHIN A SEALED CONTAINER FOR A LOOM

[75] Inventors: Masashi Toda; Hiroshi Miyake; Hironori Ito; Shigeto Ozaki; Atsuhisa Ando, all of Kariya, Japan

[73] Assignee: Kabushiki Kaisha Toyoda Jidoshokki Seisakusho, Kariya, Japan

[21] Appl. No.: 162,068

[22] PCT Filed: Jun. 11, 1992

[86] PCT No.: PCT/JP92/00744
§ 371 Date: Apr. 7, 1994
§ 102(e) Date: Apr. 7, 1994

[87] PCT Pub. No.: WO92/22694
PCT Pub. Date: Dec. 23, 1992

[30] Foreign Application Priority Data
Jun. 11, 1991 [JP] Japan .................................. 3-139145
Jun. 12, 1991 [JP] Japan .................................. 3-140423

[51] Int. Cl.6 ........................................... D03D 51/18
[52] U.S. Cl. ................... 139/1 B; 250/559.42; 356/431; 242/534
[58] Field of Search ............... 250/563, 572; 356/431; 139/1 B, 348, 304; 242/534

[56] References Cited

U.S. PATENT DOCUMENTS

| | | | |
|---|---|---|---|
| 2,279,759 | 4/1942 | Moore | 139/1 B |
| 4,131,803 | 12/1978 | Takematsu et al. | |
| 4,643,230 | 2/1987 | Aemmer et al. | 139/1 B |
| 4,702,283 | 10/1987 | Shaw | 250/563 |
| 4,879,471 | 11/1989 | Dahlquist | 250/563 |

FOREIGN PATENT DOCUMENTS

| | | | |
|---|---|---|---|
| 4814872 | 2/1973 | Japan | 139/1 B |
| 2160957 | 6/1990 | Japan. | |
| 1112277 | 9/1984 | U.S.S.R. | 139/1 B |

*Primary Examiner*—Andrew M. Falik
*Attorney, Agent, or Firm*—Brooks, Haidt Haffner & Delahunty

[57] ABSTRACT

A cloth inspecting device on a loom for detecting abnormality in the cloth being produced has a light emitting and receiving assembly mounted within a sealed container with a transparent window facing the cloth. Drive means for the assembly is within the container and the assembly is mounted on a rail for movement along the length of the container across the width of the fabric. One or more filters are provided. A mirror is disposed opposite the container window with the cloth path therebetween. By placing the light emitting and receiving assembly in a sealed container the assembly as well as its driving mechanism is positively protected against interference by fly or dust during loom operation.

16 Claims, 12 Drawing Sheets

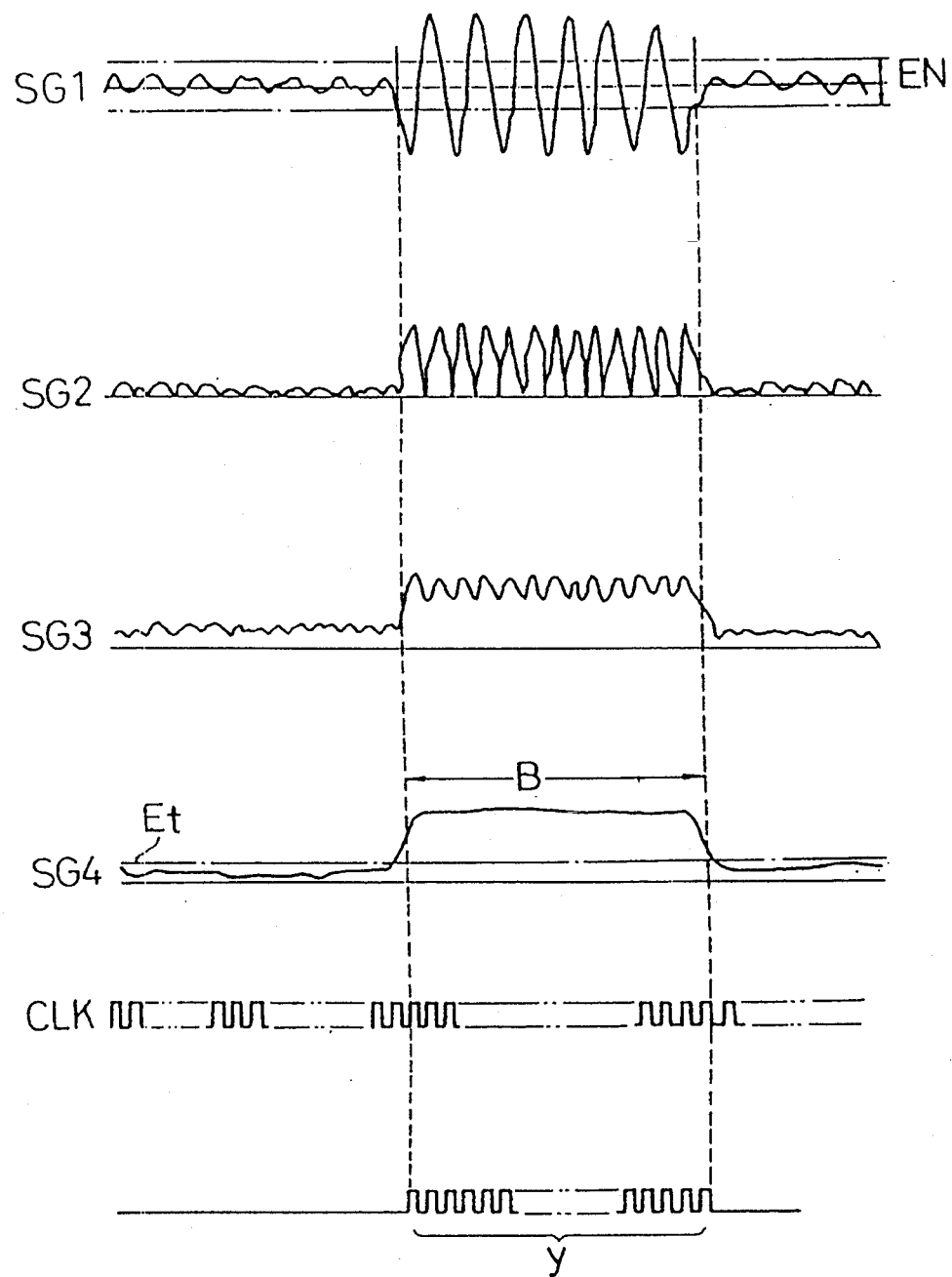

Defective portion of cloth

Defective portion of cloth

CLOTH ABNORMALITY INSPECTING DEVICE WITHIN A SEALED CONTAINER FOR A LOOM

BACKGROUND OF THE INVENTION

1. Field of the Invention

The present invention relates to a cloth inspecting device on a loom which detects abnormality of a cloth during weaving by detecting means provided with a light-receiving device that moves in the width direction of the cloth to receive light coming from the cloth within a region in the cloth moving path of the loom.

2. Description of the Prior Art

In separating a cloth inspecting step from a weaving step to determine the properness/improperness of a cloth, the decision about the properness/improperness of the cloth cannot be made unless the cloth weaving is completed. A loom is not equipped with a device to detect the improper insertion of warps between healds or reeds, or the lashing-in of warps due to entangling of upper and lower warps at the time of making an opening, if such occurs. Therefore, the operation of the loom continues in that state until weaving is complete, and this defect in the warp direction of the cloth remains until the completion of the weaving. Even if the woven cloth has no defect, it is necessary to put the cloth through a cloth inspecting step to check the properness-/improperness, inevitably deteriorating the cloth inspecting efficiency.

Conventionally, a device shown in FIGS. 15 and 16 and a device shown in FIGS. 17 and 18 have been proposed as a cloth detecting device in a loom (Japanese Unexamined Patent Publication No. Hei 2-160957). In the device shown in FIGS. 15 and 16, a cylindrical reflector 62 equal in length to or longer than the weaving width of a cloth W is provided along the width of the cloth W directly below the cloth W between reeds 60 and an expansion bar 61. A rod-shaped convex lens 63 is fitted in a cutaway provided over the entire length of the reflector 62. The reflector 62 is so provided that the convex lens 63 faces upward. A rod-shaped light source 64 is retained in a hollow portion of the reflector 62. A line sensor 65 of nearly the same length as the convex lens 63 is provided in the direction of the weaving width, directly above the reflector 62 with the cloth W therebetween, and the light-receiving surface of the line sensor 65 faces downward. A cover 66 is provided at the back of the line sensor 65, with its lower edge 66a set at the position contacting the top surface of the cloth W. Emitted light converged in line by the convex lens 63 passes through the cloth W to be received by the line sensor 65. The output signal of the line sensor 65 is compared with a set value stored in a reference fabric memory to determine the properness/improperness of the cloth. In the device shown in FIGS. 17 and 18, a cover 68 is slidably supported on a pair of guide rails 67. A threaded drive shaft 69 is engaged with the cover 68, penetrating therethrough, and is the cover 68 reciprocated at a given period by a motor 70. Retained in the cover 68 is a light-emitting apparatus, which comprises a light source 71 and a convex lens 72, and a light-receiving apparatus, which comprises a light-receiving element 73 and a convex lens 74. These light-emitting and light-receiving apparatuses run and scan over the entire weaving width area of the cloth W in accordance with the reciprocation produced by the threaded drive shaft 69. The lower edge of the cover 68 is set apart from but in the vicinity of the top surface of the cloth W.

Considerable fiber dust fly or dust is drifting in a factory where a loom is placed, and will stick on a light-receiving device, causing noise on a detection signal from the light-receiving device, unless the light-receiving device is covered with a cover. In the device shown in FIGS. 15 and 16, the line sensor 65, which is the light-receiving device, is covered with the cover 66 and the lower edge 66a of the cover 66 is set in contact with the top surface of the cloth W, making it difficult for fly or dust to stick on the light-receiving device. At the time the lower edge 66a moves away from the top surface of the cloth W due to vibration of the cloth W, however, fly or dust may enter the cover 66. To prevent this, it can possibly be considered that the lower edge 66a is pressed against the top surface of the cloth W, which will however increase the frictional resistance to the lower edge 66a. Further, this device requires the line sensor 65 equal in length to or longer than the weaving width of the cloth W, raising a problem of increasing the manufacturing cost.

In the device shown in FIGS. 17 and 18, there is a clearance between the cover 68 which covers the light-emitting and light-receiving apparatuses and the top surface of the cloth W, so that fly or dust gets in the container portion of the light-emitting and light-receiving apparatuses, thus dropping the cloth inspecting precision. Further, fly or dust are deposited on the threaded drive shaft 69 that drives the cover 68, and obstructs the driving of the cover 68. Furthermore, the cover 68, which reciprocates in the width direction of the cloth W, may be collided with another object by an unexpected accident.

It is therefore an object of the present invention to provide a cloth inspecting device on a loom, which will surely protect detecting means that runs in the direction of the weaving width of a cloth during weaving to optically detect a defect of the cloth, allows the detecting means to smoothly run without being influenced by fly or dust, and surely prevents fly or dust from sticking on a light-receiving device to reduce fly- or dust-originated noise on a detection signal, thus ensuring cloth inspection with a smaller detection error.

SUMMARY OF THE INVENTION

To achieve the above object, according to this invention, there is provided a cloth inspecting device on a loom, which detects abnormality of a cloth by detecting means provided with a light-receiving device that moves in the width direction of the cloth to receive light emitted on the cloth at a position corresponding to the cloth moving path of the loom, wherein the detecting means is placed in a sealed container with a window formed of a transparent member, in such a way as to be able to reciprocate in a lengthwise direction of the container, and the container is securely provided at a position corresponding to the cloth moving path in such a way that the lengthwise direction of the container is parallel to the width direction of the cloth and that the window faces the cloth. As the detecting means is retained in the sealed container, the detecting means is completely protected, and fly or dust is prevented from sticking on the detecting means. The detecting means may be provided so as to be able to run on a rail located in the container so that it can move when driven by a belt put around pulleys provided at both ends of the container.

It is preferable that the detecting means includes a light-emitting device for emitting light in a cloth inspecting area of a cloth, and a light-receiving device for receiving reflected light from the cloth inspecting area. When a filter is provided in the light-receiving device, noise on a detection signal is small and a detection error becomes small.

As a filter constituting the light-receiving device, a plurality of filters are provided each of which has a plurality of light-receiving elements, with each filter having a different pattern of spacing or pitch between the respective light-receiving elements. The detecting means may be provided with selector means for selecting that filter from among those filters which is suitable from which to obtain cloth inspection information in association with a warp pitch of a cloth. The plurality of filters may be provided on the same light-receiving device or may be provided on a plurality of light-receiving devices which respectively receive incident light rays separated by an optical system for separating incident light from the cloth inspecting area into at least two parts. In this case, a filter suitable to obtain cloth inspection information in association with the warp pitch of a cloth is selected from a plurality of filters to thereby positively attain cloth inspection information with a smaller detection error.

With a structure wherein the container is arranged in contact with a cloth, the vibration of a cloth is suppressed and the noise of a detection signal originating from the vibration of the cloth becomes smaller. A reflector may be arranged so as to face the container with a cloth therebetween. The reflector may be arranged so as to entirely cover the window of the container, and may be arranged in contact with the cloth. With the reflector provided, the light from the cloth inspecting area that provides the detection signal is substantially transmitted light, so that the difference between the intensities of output signals corresponding to the proper portion and improper portion of the cloth is great, thus reducing a detection error.

The container may be arranged below the cloth passing position. In this case, it does not interfere with recovering work near the cloth fell at the time the weft is mis-inserted and the warp is cut off, or the maintenance of reeds or the like.

BRIEF DESCRIPTION OF THE DRAWINGS

FIG. 5 is a waveform chart showing the order in which the output signal of a differential amplifier is rectified;

DESCRIPTION OF THE PREFERRED EMBODIMENTS

The present invention will now be described in detail referring to the accompanying drawings.

Embodiment 1

Figure 1:
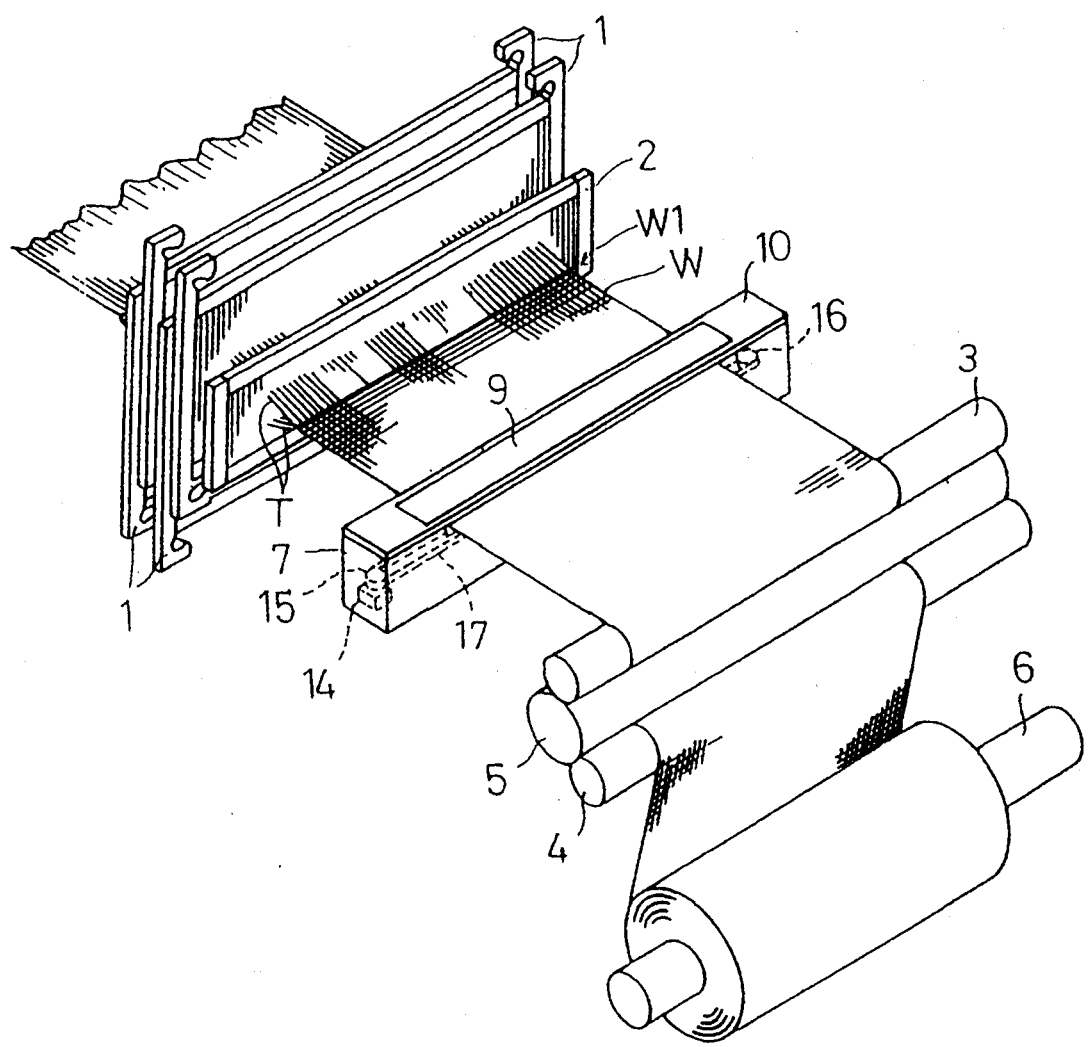
FIG. 1 is a schematic perspective view showing a cloth inspecting device according to a first embodiment installed in a loom.

A first embodiment of the present invention will now be described with reference to FIGS. 1 through 5. As shown in FIG. 1, the opening of warps T is formed by the opening movement of a heald frame 1 which constitutes an opening device. A weft inserted through the opening of the warps T is hit against a cloth fell W1 of a cloth W, forming the cloth W. The cloth W is pulled at a given speed via an expansion bar 3 by the cooperated pulling action of a press roller 4 and a surface roller 5, which constitute a cloth pulling section, and is taken up on a take-up roller 6.

A container 7, as a retaining body, equal to or larger in length than the width of the cloth W is disposed in parallel to the width direction of the cloth W, directly below a cloth passing position between the cloth fell W1 and expansion bar 3. Provided at the top of the container 7 is a window 8 (shown in FIG. 2) equal to or larger in length than the width of the cloth W, and the window 8 is formed of a plate made of a transparent material, such as glass or a synthetic resin. A cover 10 having a reflecting plate 9 as a reflector, which covers the entire window 8 through the cloth W, is detachably attached to the top of the sealed container 7. That side of the reflecting plate 9 which faces the window 8 is mirror-finished. The container 7 is disposed in contact with the bottom of the cloth W, and the reflecting plate 9 is placed in contact with the top of the cloth W. That is, the cloth W moves in a cloth inspecting area while being held between the container 7 and the reflecting plate 9.

Figure 2:
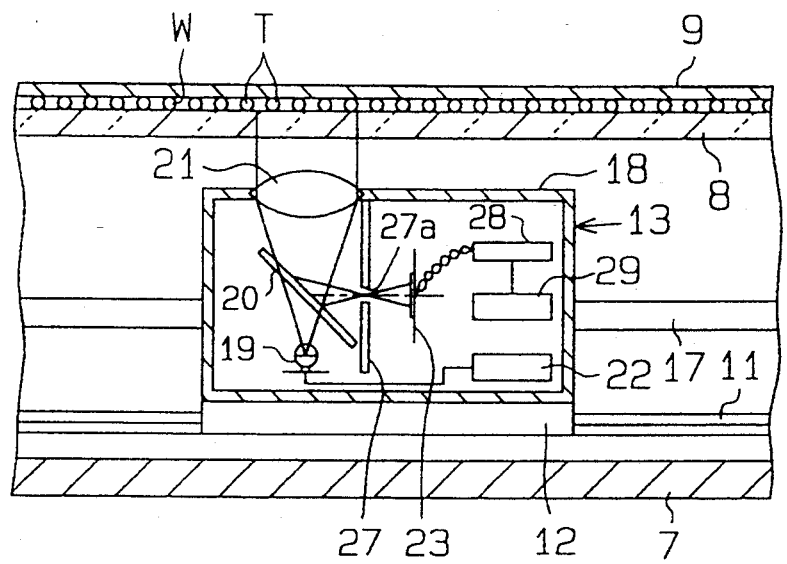
FIG. 2 is a partial cross-sectional view of the inspecting device of FIG. 1.

As shown in FIG. 2, a rail 11 is fixed in the container 7 at the bottom thereof, in the lengthwise direction of the container 7 (right and left directions in FIG. 2). A detecting means in the form of a sensor head 13 is supported via a sensor head carrier 12 on the rail 11 for movement along the rail 11. As shown in FIG. 1, a drive pulley 15, which is driven by a motor 14, is provided at a first end portion in the container 7, and a driven pulley 16 is provided at a second end portion therein. A belt 17 is put around both pulleys 15 and 16, and the sensor head 13 is secured to the belt 17. In accordance with the forward/backward rotation of the motor 14, the sensor head 13 is transported along the rail 11 via the belt 17 to scan in the width direction of the cloth W at a given speed.

A light-emitting device 19 as a light-emitting section is fixed, facing upward, in a box-shaped casing 18 of the sensor head 13 at the bottom thereof. A half mirror 20 is disposed above the light-emitting device 19, inclined at 45 degrees to the vertical direction, and a convex lens 21 for focusing light is disposed above the half mirror 20. The light-emitting device 19 is located at the focus position of the convex lens 21 so that emitted light from the convex lens 21 to the cloth W becomes parallel light. The light-emitting device 19 is driven by a light-emitting controller 22.

Figure 3:
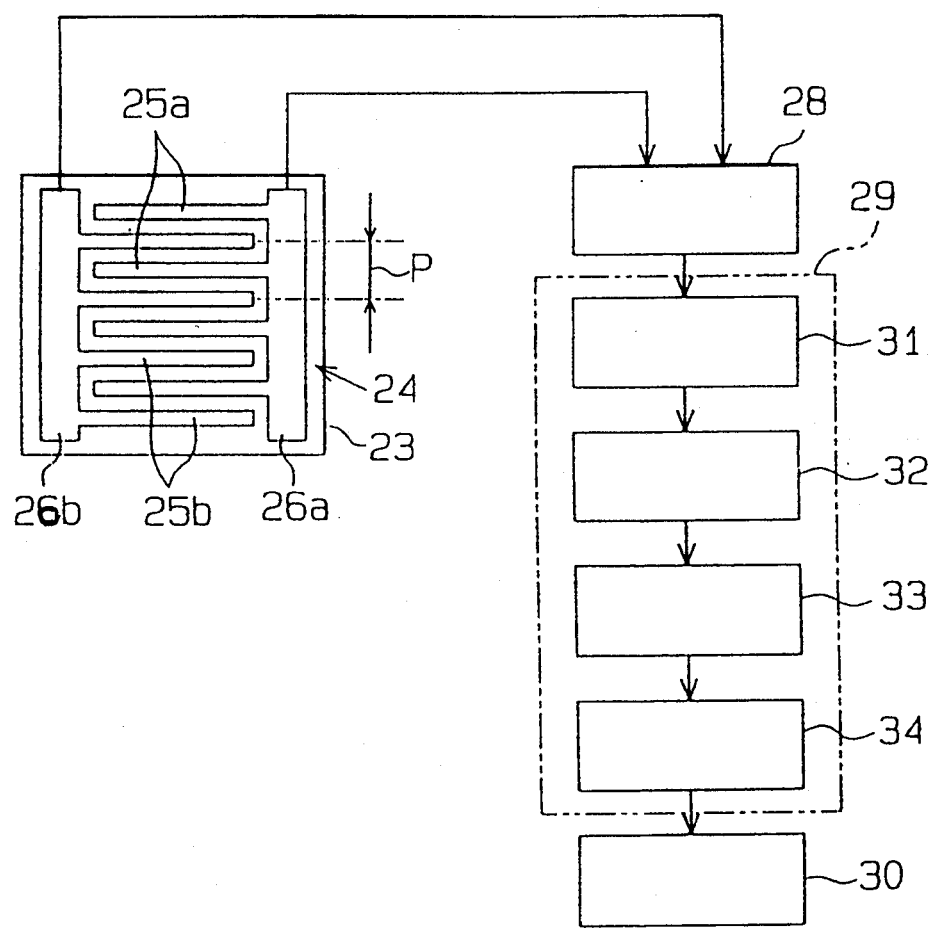
FIG. 3 is a block diagram of a circuit for processing the output signal of a filter.

Disposed at the side of the half mirror 20 is a light-receiving device 23 on which light from the cloth inspecting area or reflected light from the cloth W and the reflecting plate 9 is formed as a surface pattern. The light-receiving device 23 is provided with a filter 24. The filter 24 has a differential structure, and comprises two comb filters 26a and 26b, which have many light-receiving elements 25a and 25b arranged at a given pitch P, as shown in FIG. 3. The light-receiving elements 25a and 25b output electrical signals according to the amount of received light. The pitch P of the light-receiving elements 25a and 25b is such that light entering and leaving through the gaps between the warps T at the normal portions of the cloth simultaneously enters both light-receiving elements 25a and 25b. The light-receiving elements 25a and 25b are disposed in such a way as to face in the direction perpendicular to the moving direction of the light image focused by the convex lens 21, i.e., in parallel to the warps T of the image of the cloth W. Fixed between the half mirror 20 and the filter 24 is a light shield 27 to eliminate interference between the light-emitting device 19 and the filter 24. A small through hole 27a is formed in the light shield 27 at the focus position on the optical axis of the light, which is reflected from the cloth W and focused by the convex lens 21 and which is reflected by the half mirror 20.

The output signal of the filter 24 is output to a differential amplifier 28. The output signal of the differential amplifier 28 is processed by an output circuit 29 before being output to a determining circuit 30. The determining circuit 30 is provided outside the sensor head 13. The determining circuit may be provided inside the sensor head 13. As shown in FIG. 3, the output circuit 29 includes a full wave rectifier 31, a peak detector 32, a low-pass filter 33 and a comparator 34. The full wave rectifier 31 performs full-wave rectification on the output signal SG1 of the differential amplifier 28. The peak detector 32 holds the peak value of a signal SG2 rectified by the full wave rectifier 31, and outputs a resultant signal. The low-pass filter 33 smoothes the output signal, SG3, of the peak detector 32. The comparator 34 receives the output signal, SG4, of the low-pass filter 33, and determines if it is greater than a predetermined reference value Et (=EN/2). When the output signal is greater than the reference value Et, the comparator 34 measures the sustaining time of that state with a clock pulse CLK, and outputs a count value y as a sustaining time B to the determining circuit 30.

The determining circuit 30 compares the sustaining time B with a predetermined reference time ts, and determines that there is abnormality, such as defect warp, when the sustaining time B exceeds the reference time ts. The reference time ts is obtained in advance by test working. A decision signal of the determining circuit 30 is output to a control device for the loom or an alarm device which informs a worker of abnormality, so that when abnormality of the warps T is detected, the loom is stopped operating or the worker is informed by a lamp, a buzzer or the like.

Figure 4:
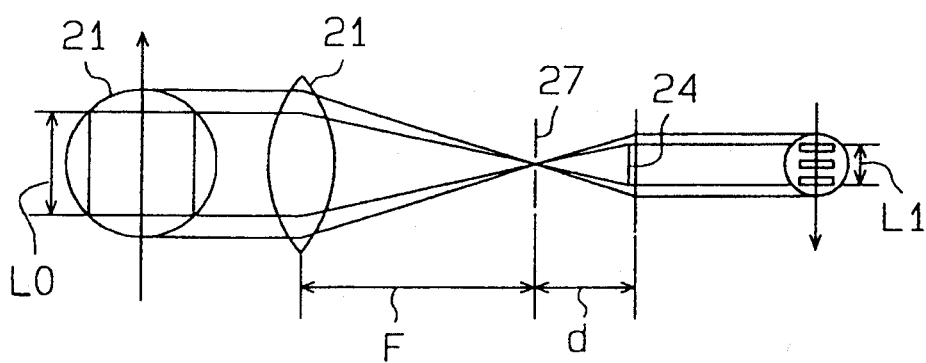
FIG. 4 is a schematic diagram showing the relationship between a lens and a light-receiving device.

The operation of the apparatus having the above structure will now be described. In inspecting the cloth W, the motor 14 is driven to move the sensor head 13 in the width direction of the cloth W at a speed v. The light-emitting controller 22 is driven to emit light from the light-emitting device 19 toward the cloth W. The light emitted from the light-emitting device 19 passes the half mirror 20, becomes parallel light through the convex lens 21, and passes through the window 8 to be irradiated on the cloth inspecting area at the back of the cloth W. The light irradiated on the cloth W is reflected directly at the back of the cloth W or by the reflecting plate 9 located above the cloth W. The reflected light passes the convex lens 21 again, and is reflected by the half mirror 20 to be formed on the filter 24 as a pattern of the cloth W. It is only the light passing the through hole 27a of the light shield 27 that reaches the filter 24. As the through hole 27a is located at the focus position of the convex lens 21, only parallel rays of the reflected light which enters the convex lens 21 passes the hole 27a to reach the filter 24. As shown in FIG. 4, given that the focus distance of the convex lens 21 is F, the distance between the focus position and the light-receiving face of the filter 24 is d, the length of an image incident to the convex lens 21 is L0 and the length of an image formed on the light-receiving face of the filter 24 is L1, an image magnification m is expressed by the following equation.

$$m = L1/L0 = d/F$$

Given that the pitch of the light-receiving elements 25a and 25b of the comb filters 26a and 26b, which constitute the filter 24, is P and the moving speed of the filter 24 is v, the output frequency f of the output signal from the differential amplifier 28 is given by the following equation.

$$f = (m/P)v = (1/P)(d/F)v$$

As the pitch P, distance d and focus distance F are constant, an output signal having a frequency proportional to the moving speed of the filter 24, or the scanning speed of the sensor head 13, v, is obtained.

The reflected light from the cloth W and the reflected light, which is reflected by the reflecting plate 9 provided at the top surface of the cloth W and returns through the gaps in the cloth W, reach the light-receiving device 23 and form images thereon. The light-receiving elements 25a and 25b provided in the light-receiving device 23 output currents corresponding to the intensities of received lights. The intensity of the reflected light from the cloth W is significantly smaller than that of the reflected light, which is reflected by the reflecting plate 9 provided at the top surface of the cloth W and returns through the gaps between the warps T of the cloth W. Therefore, the output originated from the reflected light from the cloth W becomes equivalent to noise, as compared with the output originated from the reflected light from the reflecting plate 9. The reflected light from the reflecting plate 9 at a defective portion of the cloth W has the same intensity as the reflected light coming through the gaps between the warps T at the proper portions of the cloth. At the proper portions of the cloth, however, light entering and leaving through the gaps between the warps T at the proper portions of the cloth reaches both light-receiving elements 25a and 25b at the same time, and the output signals of the light-receiving elements 25a and 25b, when subtracted from each other in the differential amplifier 28, are canceled out so that the amplitude of the output signal of the differential amplifier becomes smaller. At the defective portion of the cloth W, on the other hand, the reflected light from the reflecting plate 9 enters either the light-receiving elements 25a or 25b, and the difference in amplitudes of the output signal of the differential amplifier 28 becomes larger.

As a result, as shown in FIG. 5, when there is no abnormality in the warps T in the cloth inspecting area, the amplitude of the output signal SG1 from the differential amplifier 28 based on the output of the filter 24 has a level smaller than the predetermined level EN. When there is abnormality in the warps T, such as cut or deviation, on the other hand, the amplitude of the output signal SG1 has a level larger than the predetermined level EN. The signal sent to the output circuit 29 from the differential amplifier 28 is subjected to full wave rectification, peak holding and smoothing process in the output circuit 29. The output signal SG4 of the low-pass filter 33 is input to the comparator 34 where it is determined whether or not the signal is greater than the predetermined reference value Et. When the output signal SG4 is greater than the reference value Et, the sustaining time B of that state is measured with the clock pulse, and the count value y is output as the sustaining time B to the determining circuit 30. The determining circuit 30 determines that there is abnormality when the sustaining time B is larger than the reference time ts. When the fluctuating level of the output signal of the differential amplifier 28 is smaller than the predetermined level, the sustaining time B is not measured in the comparator 34. As a result, no clock pulse will be sent to the determining circuit 30 from the comparator 34, so that the determining circuit 30 determines that there is no abnormality.

As the sensor head 13 is accommodated in the container 7 and the window 8 is sealed with a transparent member, dust or fly will not be deposited on the rail 11, permitting the sensor head 13 to always run smoothly. Further, the sensor head 13 will not be collided with another object by an unexpected accident. Furthermore, fly or dust is surely prevented from sticking on the light-emitting device 19, light-receiving device 23 or the optical system, equipped in the sensor head 13, and noise on the detection signal originated from fly or dust becomes smaller, thus ensuring cloth inspection with less detection error.

If the sensor head 13 is reciprocated for scanning in a specific narrow area after repairing warp cut, not over the entire width of the cloth W always, a specific portion can be preponderantly inspected at the time of, for example, checking if there is wrong insertion of warps between the healds or reeds.

As the light-receiving elements 25a and 25b of the filter 24 are arranged in the same direction as the image of the warps T, when there is defective warp in the cloth W, the irregularity of the warps T is continuously detected by the light-receiving elements 25a and 25b and an output signal different from that for the proper portion is continuously generated. Thus, it is possible to determine a defect by the output signal of the filter 24 alone.

Since, at the position corresponding to the cloth inspecting area, the cloth W is held between the reflecting plate 9 and the container 7 and moves while in contact with both, the vibration of the cloth W in the cloth inspecting area is suppressed, thus eliminating vibration-oriented noise on the detection signal. Further, it is difficult for dust or fly to enter the cloth inspecting area of the cloth W, and dust or fly, even if enters there, are removed outside the cloth inspecting area in accordance with the movement of the cloth W. The cloth W serves to polish the mirror surface of the reflecting plate 9, so that at the time of cloth inspection, the mirror surface is always kept at good reflecting condition.

As the container 7 is located under the cloth W, it does not interfere with a recovering work near the cloth fell at the time the weft is mis-inserted and the warp is cut off, or with the maintenance of reeds or the like. Since the reflecting plate 9 is located above the cloth W at a position corresponding to the cloth inspecting area in the apparatus according to this embodiment, light entering the cloth inspecting area from the surface side of the cloth W is only the reflected light from the reflecting plate 9, and will not be influenced by disturbing light. Therefore, light-disturbance oriented noise will surely be removed.

The intensity of the reflected light from the cloth W is significantly smaller than that of the reflected light, which is reflected by the reflecting plate 9 and returns through the gaps between the warps T of the cloth W. If it is not provided with the reflecting plate 9 and a defective portion of the cloth W is detected based on the reflected light from the cloth W, the difference between the output by the reflected light from the cloth W and the output in the case of no reflected light is small, so that a detection error is likely to occur. With the provision of the reflecting plate 9, however, a defective portion of the cloth W is detected based on the reflected light from the reflecting plate 9, so that the difference between the output at a defective portion of the cloth W and the output at a proper portion of the cloth W is large, thus suppressing erroneous detection.

Embodiment 2

The second embodiment will now be described referring to FIGS. 6 through 10. The apparatus according to this embodiment differs from the above-described embodiment in the filter constituting the light-receiving device 23 and the circuit structure of processing its signal.

Figure 6:
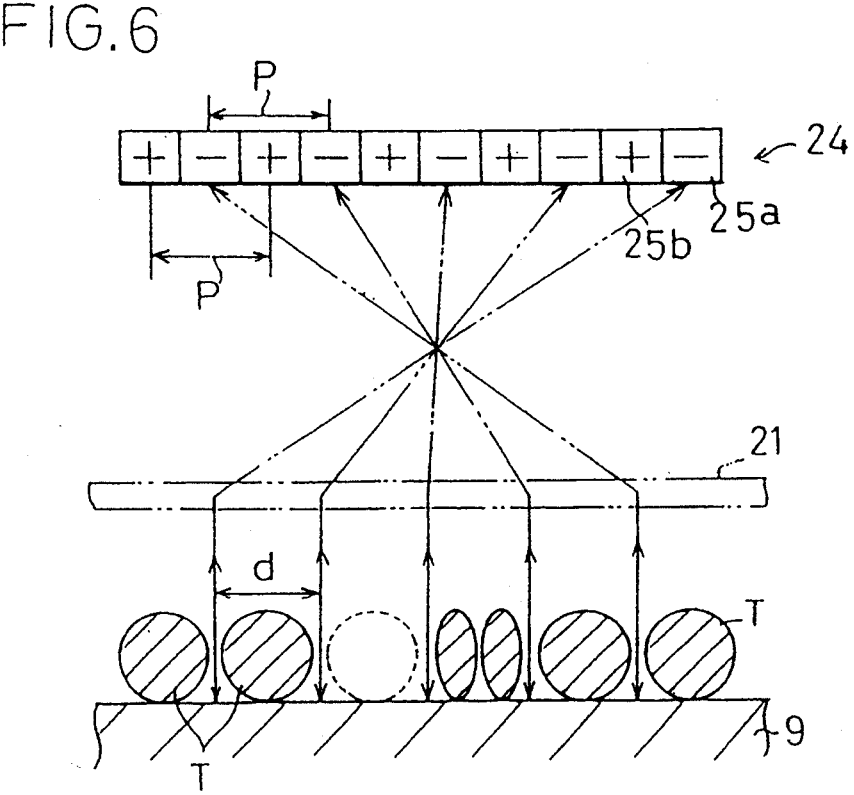
FIG. 6 is a diagram for explaining the relationship of images formed between the pitch of a light-receiving element and a warp pitch.
Figure 7:
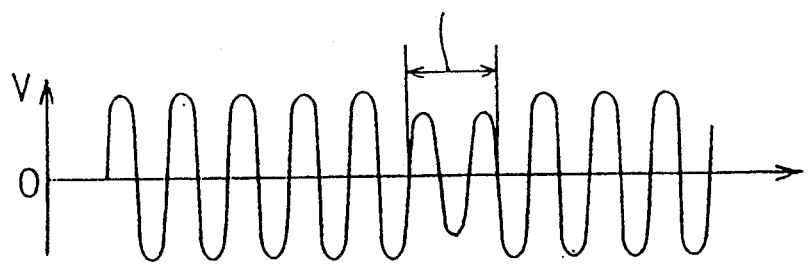
FIG. 7 is a diagram showing the output signal of the differential amplifier for one mode of operation of the inspection device described with reference to FIG. 6.

The cloth inspecting device using a filter detects asymmetry appearing on a cloth as a defect, and uses, as a signal, a change in amplitude occurring on the output (frequency signal) of the filter due to a change in the amount of received light. It is considered that the case where, for example, an image of a cloth whose warps T has a pitch d is formed on the filter 24 whose light-receiving elements 25a and 25b has a pitch P, with a magnification m, as shown in FIG. 6. When the pitch P equals to md or an integer multiplication thereof, at the time light entering or leaving through the gaps between the warps T at the proper portions of the cloth enters one of the light-receiving elements, 25a, the light entering or leaving through the gaps between the warps T will not enter the other light-receiving element 25b. As a result, even both lights are subtracted from each other, the difference remains as it is, increasing the amplitude of the output signal of the differential amplifier. At the defective portion of the cloth, the light enters both light-receiving elements 25a and 25b at the position corresponding to the defective portion, making the difference between both lights smaller. Thus, the output signal of the differential amplifier becomes as shown in FIG. 7, and the difference between the amplitudes of the output signals corresponding to the proper portion and defective portion of the cloth becomes smaller, thus lowering the detection accuracy.

Figure 8:
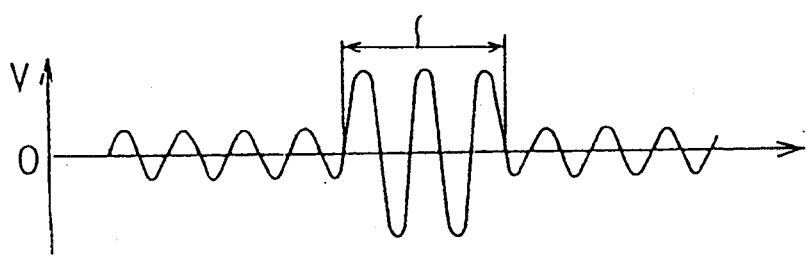
FIG. 8 is a diagram showing the output signal of the differential amplifier for another mode of operation of the inspection device described with reference to FIG. 6.

When the pitch P does not equal to md or an integer multiplication thereof, the light leaving and entering through the gaps between the warps T enters both the light-receiving elements 25a and 25b at the proper portion of the cloth. And, the output signals of the light-receiving elements 25a and 25b, when subtracted from each other in the differential amplifier 28, are canceled out so that the amplitude of the output signal of the differential amplifier becomes smaller. At the defective portion of the cloth, on the other hand, the difference between the amount of lights entering both light-receiving elements 25a and 25b increases. Thus, the output signal of the differential amplifier becomes as shown in FIG. 8, and the difference between the amplitudes of the output signals corresponding to the proper portion and defective portion of the cloth is large, thus suppressing erroneous detection.

In the case where a single filter is provided with the sensor head 13, therefore, when the relationship between the warp pitch of a cloth and the pitch of the light-receiving elements or the like corresponds to condition of impairing the aforementioned detection accuracy, a detection error would occur. To suppress erroneous detection, it is necessary to adjust the pitch of the light-receiving elements or the image magnification of the optical system. To change the pitch of the light-receiving elements, many specifications with different pitches should be prepared, and the detachment/attachment involved replacement takes time. Further, it is difficult to change and adjust the magnification of the optical system, and there is a chance of touching the optical parts by hands and staining the optical parts, thus reducing the performance.

The apparatus of this embodiment is designed to always obtain a detection result with a less error irrespective of the warp pitch of a cloth.

Figure 9:
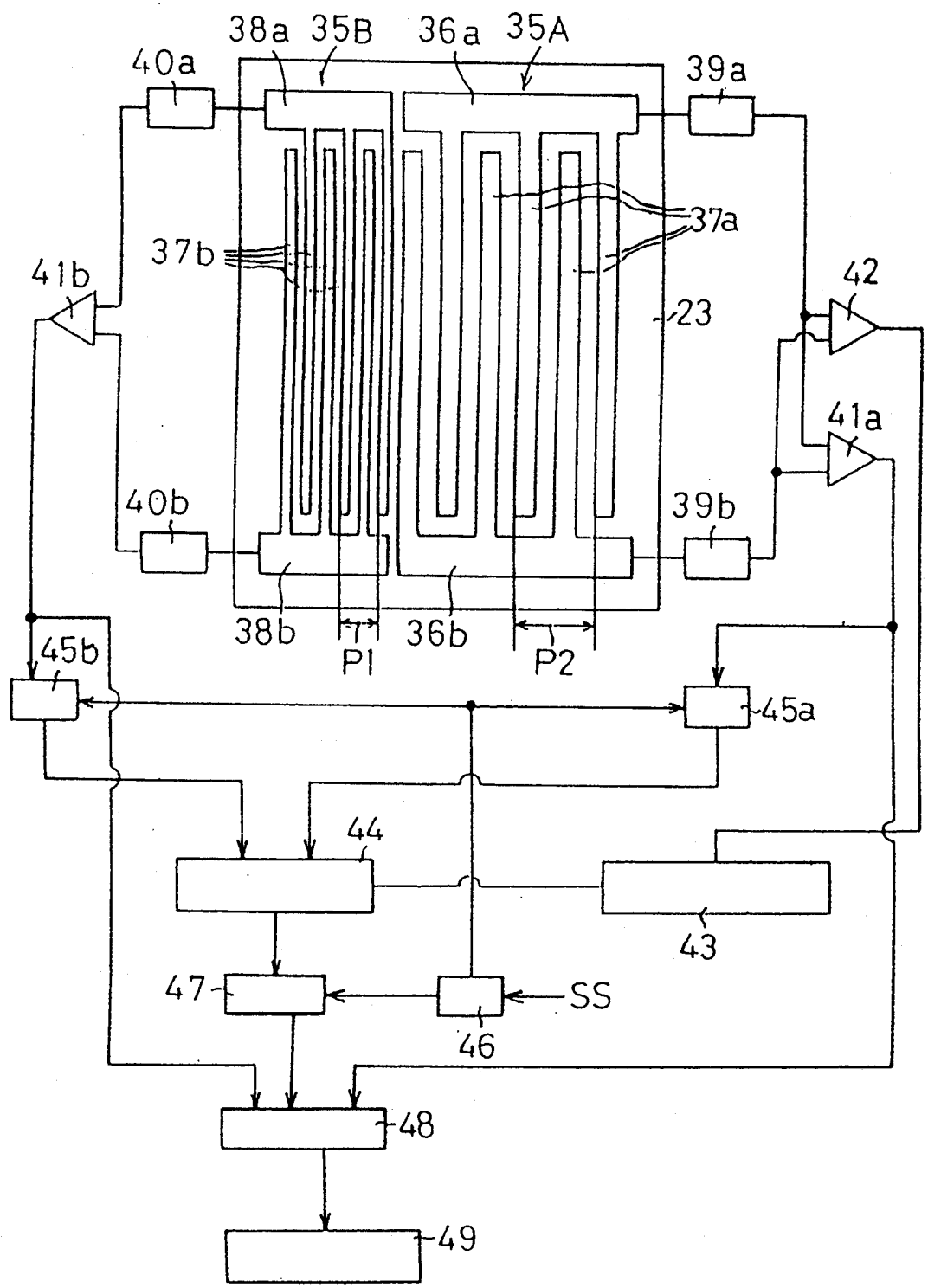
FIG. 9 is a block diagram of a second embodiment.

As shown in FIG. 9, the light-receiving device 23 on which light from the cloth inspecting area is formed as a surface pattern of a cloth has two filters 35A and 35B. Both filters 35A and 35B have a differential structure. The first filter 35A comprises a pair of comb filters 36a and 36b each of which has light-receiving elements 37a arranged at a pitch P2. The second filter 35B comprises a pair of comb filters 38a and 38b each of which has light-receiving elements 37b arranged at a pitch P1.

Connected to the comb filters 36a and 36b of the first filter 35A are current-to-voltage converters 39a and 39b which convert currents generated in the light-receiving elements 37a to voltages. Connected to the comb filters 38a and 38b of the second filter 35B are current-to-voltage converters 40a and 40b which convert currents generated in the light-receiving elements 37b to voltages. Differential amplifiers 41a and 41b are respectively connected to the current-to-voltage converters 39a and 39b, and 40a and 40b. Connected to the current-to-voltage converters 39a and 39b, connected to the first filter 35A, is an adder 42 to which a reference value generator 43 is connected. The reference value generator 43 estimates the noise level to be expected, based on an input signal from the adder 42, and outputs a decision reference voltage to a selector 44.

Integrators 45a and 45b detect the output signals of the differential amplifiers 41a and 41b, integrate their levels over a given period, and send the results to the selector 44. The integrators 45a and 45b start the integration based on the signal from a reset circuit 46 at the time of filter selection. The selector 44 compares the signals from both integrators 45a and 45b with the output of the reference value generator 43, and outputs a signal for selecting one of the two filters 35A and 35B to an output circuit 47. The output circuit 47 converts the signal from the selector 44 to a signal for driving a switch 48, and sends it to the switch 48. The switch 48 is designed to output one of the output signals of the differential amplifiers 41a and 41b to a signal processor 49 based on the output signal of the output circuit 47. The adder 42, reference value generator 43, selector 44, integrators 45a and 45b, reset circuit 46, output circuit 47 and switch 48 constitute selecting means for selecting a filter suitable to obtain cloth inspection data.

The signal processor 49 has a structure which is a combination of the output circuit 29 and determining circuit 30 of the first embodiment. In other words, the signal processor comprises a full wave rectifier, a peak detector, a low-pass filter, a comparator and a determining circuit. The full wave rectifier performs full wave rectification on one of the output signals of the differential amplifiers 41a and 41b, and the other circuits function in the same way as the corresponding circuits of the first embodiment.

The operation of the apparatus constituted in the above manner will be described below. As cloth inspection starts, light from the cloth inspecting area enters the light-receiving device 23, and the output signals of the filters 35A and 35B, or the output signals of the comb filter pairs 36a and 36b, and 38a and 38b, are input to the first differential amplifier 41a and the second differential amplifier 41b via the current-to-voltage converters 39a and 39b and 40a and 40b. The difference signal between the comb filter pair 36a and 36b is output to the integrator 45a and the switch 48 from the first differential amplifier 41a, and the difference signal between the comb filter pair 38a and 38b is output to the integrator 45b and the switch 48 from the second differential amplifier 41b. The output signals from the current-to-voltage converters 39a and 39b are added together in the adder 42, and the resultant signal is input to the reference value generator 43. Based on the input signal from the adder 42, the reference value generator 43 outputs a reference voltage, which will be a reference value, to the selector 44.

A start signal SS from the loom's main body is input to the reset circuit 46 at the time the cloth inspection starts, and the reset circuit 46 outputs a reset signal to the output circuit 47, releasing the output holding state of the output circuit 47. The start signal is output to both integrators 45a and 45b from the reset circuit 46, and the integrators 45a and 45b integrate the outputs from the respective differential amplifiers 41a and 41b over a given time t. The results of the integration are output to the selector 44. The selector 44 compares the output signals with the reference value from the reference value generator 43.

Figure 10:
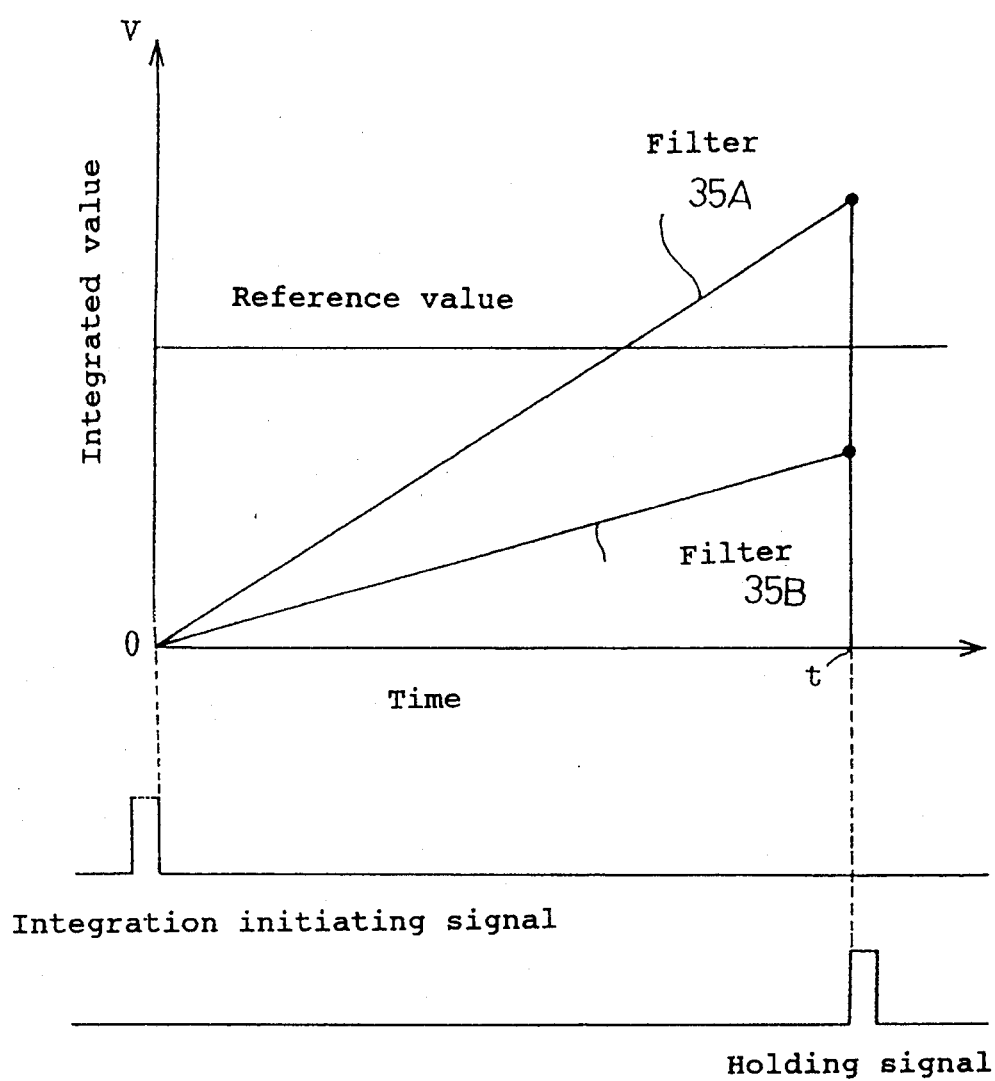
FIG. 10 is a diagram illustrating the operation of the embodiment of FIG. 9.

When the value of the integration on the side of the first filter 35A is greater than the reference value as shown in FIG. 10, for example, the selector 44 determines the first filter 35A as inappropriate and the second filter 35B as appropriate. Then, the selector 44 outputs a signal indicating the second filter 35B (e.g., 2-bit data "10") to the output circuit 47. In accordance with the held signal from the reset circuit 46, the output circuit 47 fixes the data from the selector 44 indicating the selection of the second filter 35B. The output circuit 47 also outputs, to the switch 48, a signal to set the switch 48 in a state to output only the output of the second filter 35B, i.e., only the output signal of the second differential amplifier 41b, to the signal processor 49. Then, the switch 48 is switched to the state to output the output signal of the second differential amplifier 41b to the signal processor 49, and cloth inspection is carried out in that condition.

There are three results of comparison between the input signals from both integrators 45a and 45b and the reference value: the input signal from one of the integrators 45a and 45b greater than the reference value, both input signals smaller than the reference value, and both input signals greater than the reference value. Of those results, both input signals becoming greater than the reference value is in the case where abnormality occurs in the apparatus. When the input signal from one of the integrators 45a and 45b is greater than the reference value, the filter which has provided a signal smaller than the reference value becomes an appropriate filter. When both input signals are smaller than the reference value, both filters 35A and 35B become appropriate, but the smaller the noise is, the smaller the integrated value becomes, and a smaller integrated value can suppress erroneous detection better. When both input signals are smaller than the reference value, therefore, the selector 44 selects the filter corresponding to that integrator which provides a lower level, and outputs an instruction signal to the output circuit 47. 2-bit data "10" is output when indicating the second filter 35B as mentioned above, 2-bit data "11" is output when indicating the first filter 35A, and 2-bit data "01" is output when both filters 35A and 35B are inappropriate.

When there is no abnormality in the apparatus, therefore, the output signal from that one of the two filters 35A and 35B which is more appropriate for cloth inspection is input to the signal processor 49 to always provide cloth inspection data with a less detection error. Regardless of the warp pitch of the cloth, cloth inspection data with a less detection error can surely be obtained based on the output signal of that filter which is suitable to obtain the cloth inspection data in association with the warp pitch of the cloth, without adjustment of the optical system of the cloth inspecting device or replacement of the light-receiving device by an operator. Further, it is unnecessary to prepare many light-receiving devices with different specifications and is thus possible to reduce the manufacturing cost.

According to this embodiment, as a plurality of filters 35A and 35B are provided on a single light-receiving device 23, a plurality of light-receiving devices need not be provided, so that the manufacturing cost can be suppressed.

Three or more filters may be provided on the light-receiving device 23, and the current-to-voltage converters, differential amplifiers and integrators may be provided in accordance with the quantity. In this case, cloth inspection is executed with a filter more suitable for the cloth W. The selecting means for selecting the optimal filter from a plurality of filters may have such a structure that a memory device where data indicating which filter is suitable for which type (warp pitch) of a cloth is stored may be provided and a signal indicating an appropriate filter is output to the output circuit 47 according to the data stored in the memory device, based on the type of the cloth input through an input device. This data is obtained in advance by tests. In this case, the adder 42, reference value generator 43, selector 44, integrators 45a and 45b and reset circuit 46 become unnecessary.

Embodiment 3

Figure 11:
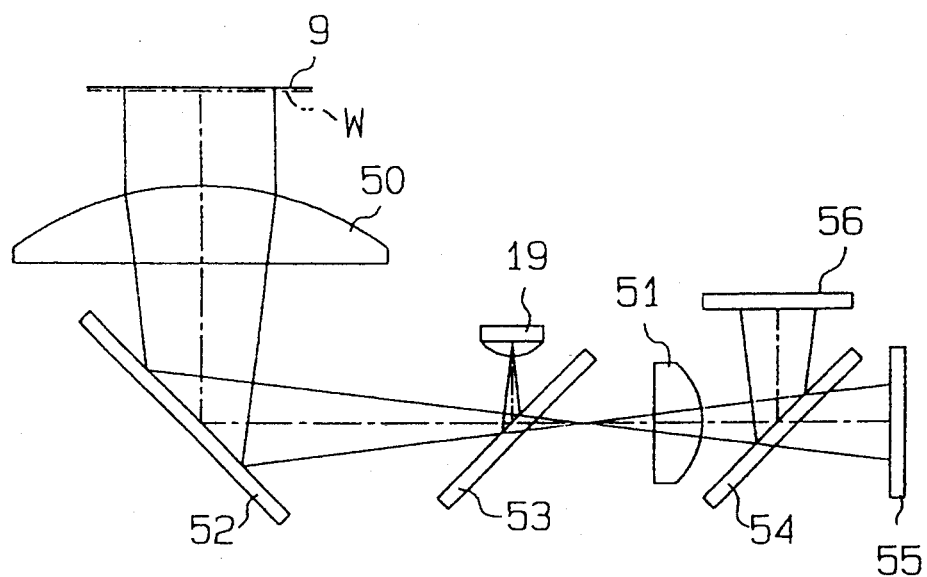
FIG. 11 is a schematic diagram showing the relationship between an optical system and a light-receiving device of a third embodiment.
Figure 12:
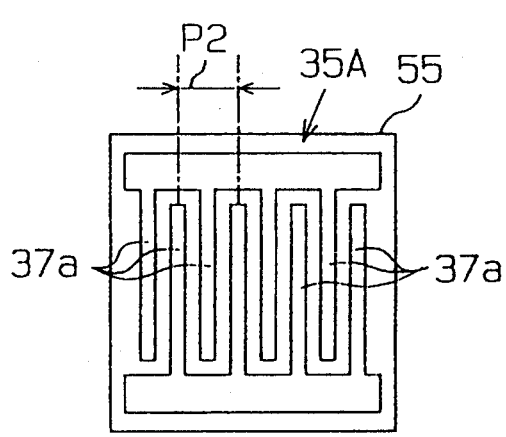
FIG. 12 is a diagram showing a filter provided in one of the light-receiving devices of FIG. 11.
Figure 13:
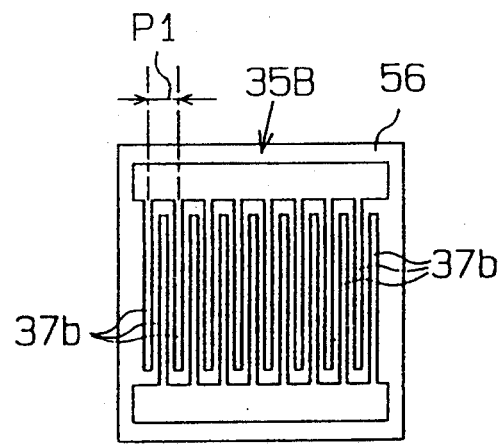
FIG. 13 is a diagram showing a filter provided in the other of the light-receiving devices of FIG. 11.

The third embodiment will now be described with reference to FIGS. 11 through 13. This embodiment differs from the previous embodiment in that incident light from the cloth inspecting area is separated to two by an optical system, and the separated incident lights are respectively received by separate light-receiving devices. As shown in FIG. 11, the optical system comprises two convex lenses 50 and 51, one mirror 52, and two half mirrors 53 and 54. The mirror 52 is disposed, inclined at 45 degrees to the vertical direction, below the first convex lens 50 placed opposite the reflecting plate 9. The first half mirror 53 is disposed by the mirror 52 at an angle of 90 degrees to the mirror 52. The light-emitting device 19 is disposed, facing downward, above the first half mirror 53.

The second half mirror 54 is disposed by and in parallel to the first half mirror 53, and the second convex lens 51 is located between the half mirrors 53 and 54. A first light-receiving device 55 and a second light-receiving device 56 are respectively disposed by and above the second half mirror 54, at an angle of 45 degrees to the half mirror 54. As shown in FIG. 12, the first filter 35A having the light-receiving elements 37a of the pitch P2 is provided above the first light-receiving device 55. As shown in FIG. 13, the second filter 35B having the light-receiving elements 37b of the pitch P1 is provided above the second light-receiving device 56.

The light emitted from the light-emitting device 19 is reflected by the first half mirror 53 and the mirror 52 to be guided to the first convex lens 50 through which it becomes parallel light to be irradiated on the cloth inspecting area of the cloth W. The reflected light from the reflecting plate 9 and the cloth W passes the first convex lens 50 again, is reflected by the mirror 52 and passes the first half mirror 53 and the second convex lens 51. The light having passed the second convex lens 51 is divided to two by the second half mirror 54, which reach the light-receiving devices 55 and 56. That is, the reflected light from the same cloth inspecting area is received by the light-receiving devices 55 and 56 having the filters 35A and 35B of different pitches P1 and P2 (P1≠P2). As in the previous embodiment, therefore, cloth inspection data with a less detection error is obtained by selecting the output signal from the filter of one of the light-receiving devices.

According to this embodiment, if the areas of the individual light-receiving devices 55 and 56 are set equal to the area of the light-receiving device 23 of the second embodiment, the number of the light-receiving elements 37a and 37b of the filters 35A and 35B provided on the light-receiving device can be increased.

This can suppress erroneous detection more than the previous embodiment.

Figure 14:
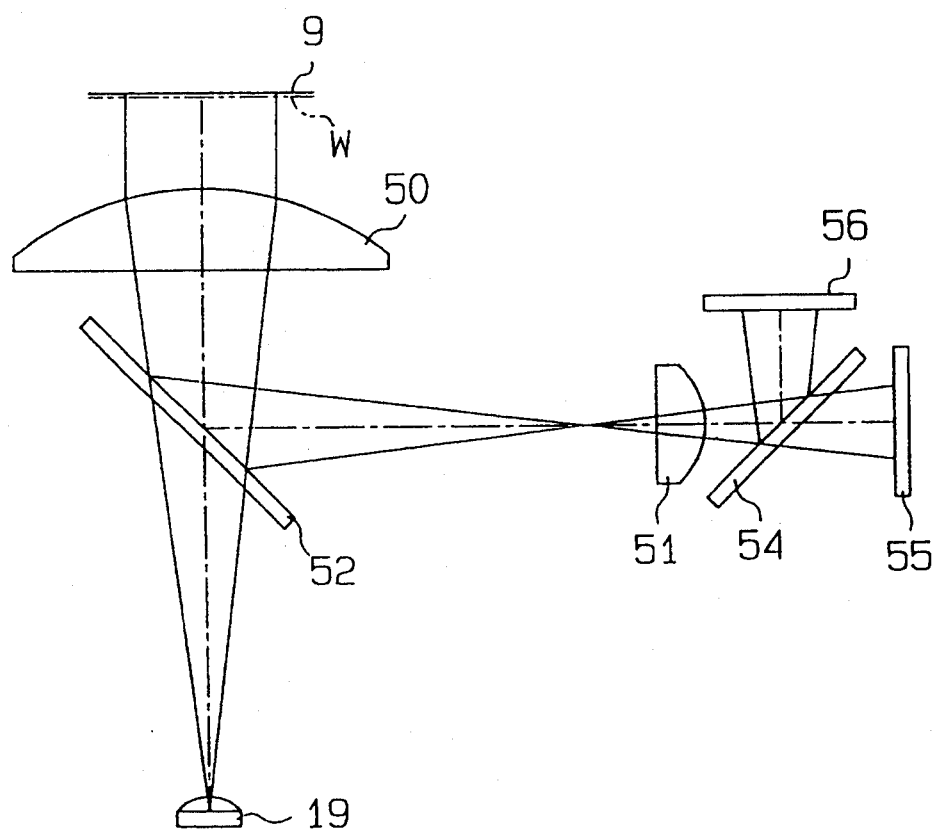
FIG. 14 is a schematic diagram showing the relationship between an optical system and a light-receiving device according to a modification of the embodiment of FIG. 11.
Figure 15:
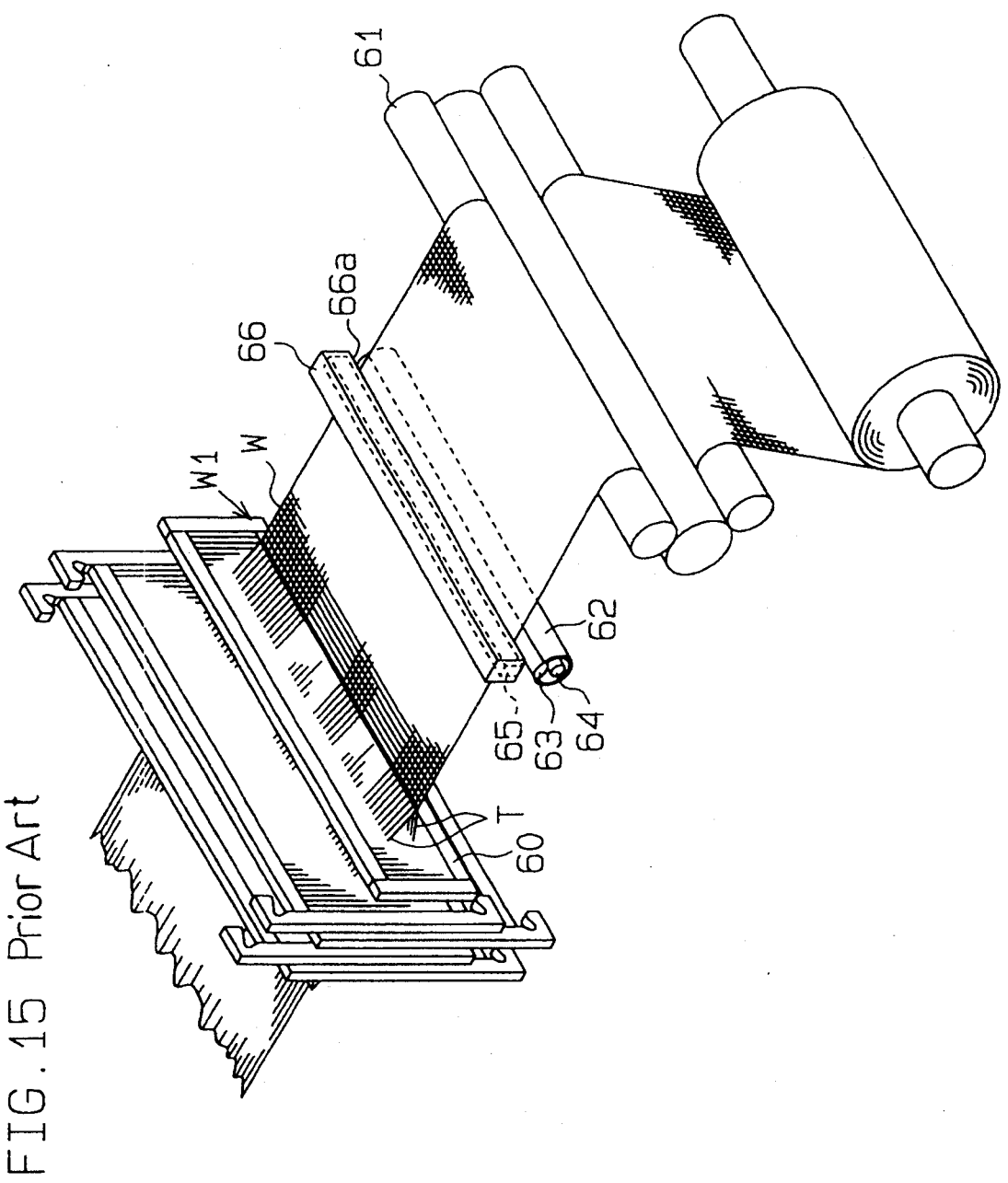
FIG. 15 is a schematic perspective view of a conventional device.
Figure 16:
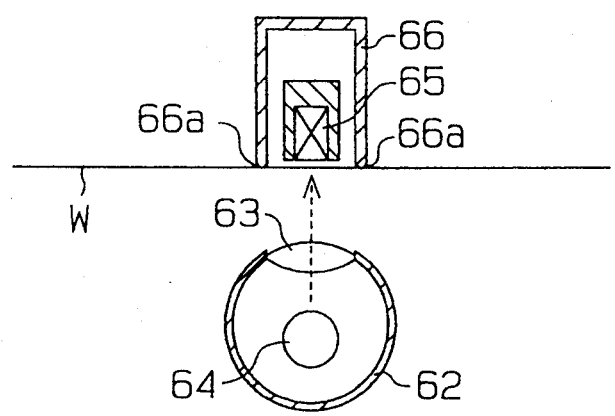
FIG. 16 is a cross-sectional view of the detecting device of FIG. 15.
Figure 18:
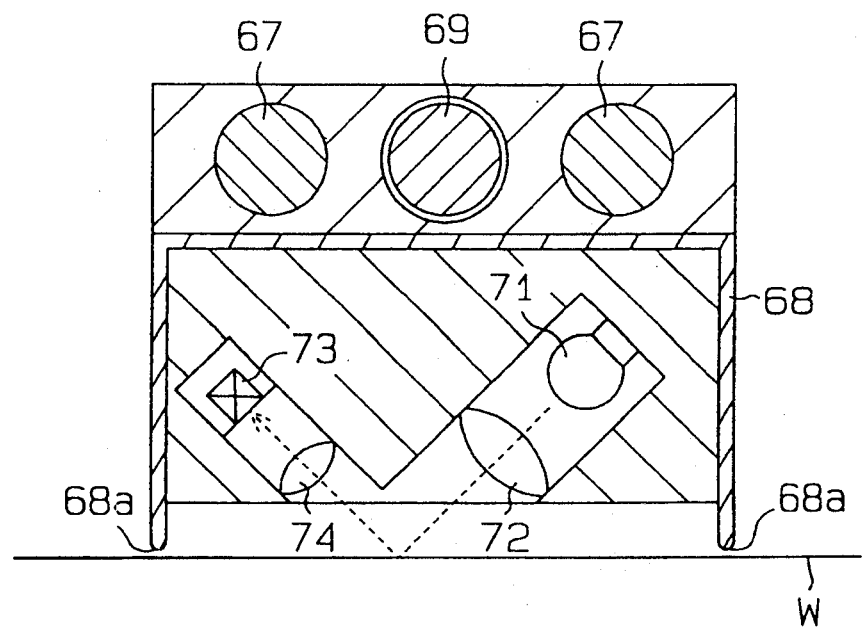
FIG. 18 is a cross-sectional view of the detecting device of FIG. 17.
Figure 17:
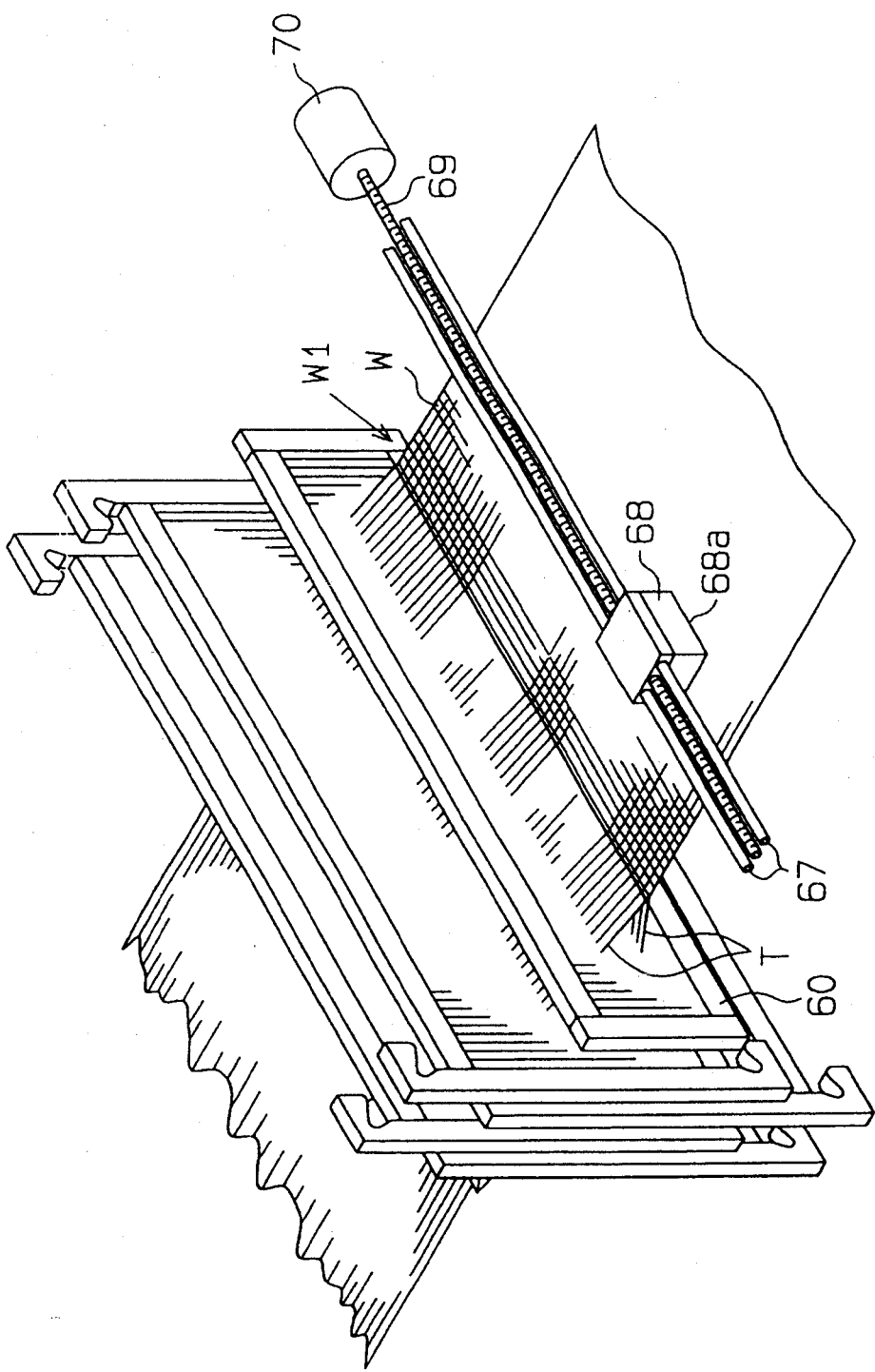
FIG. 17 is a schematic perspective view of another conventional device.

As the optical system for separating the reflected light from the cloth inspecting area to two, the first half mirror 53 may be disposed under the first convex lens 50, with the light-emitting device 19 positioned under the mirror, as shown in FIG. 14. In this case, the mirror 52 becomes unnecessary. In either structure, the second convex lens 51 is not essential and may be omitted. The reflected light may be separated to more than two, and the number of the light-receiving devices may be increased accordingly, or a plurality of filters with different pitches may be provided on each of a plurality of light-receiving devices. In this case, it is possible to select a filter which is more appropriate for a cloth.

It should be noted that this invention is not limited to the above embodiments. For instance, a rod-shaped lens may be employed as the convex lens 21 instead of a circular lens, the light-emitting device 19 may be disposed at a position other than the focus of the convex lens 21. The filter need not be a comb filter, and has only to include at least one set of light-receiving elements. Although the output signal of the differential amplifier 28 is subjected to wave shaping by the full wave rectifier, peak detector, low-pass filter, comparator and the like before being output to the determining circuit, another wave-shaping method may also be employed. Instead of providing the differential amplifier 28, a single comb filter may be provided so that its output signal is directly output to the output circuit 29, or a photoelectric converting element (e.g., a line sensor or a photodiode) other than the filter may be used in the light-receiving device.

The container 7 may be disposed above a cloth so that the sensor head 13 performs scanning above the cloth W, or the container 7 may be disposed between the press roller 4 and the take-up roller 6. The container 7 or the reflecting plate 9 or both may be disposed not in contact with the cloth W, or the reflecting plate 9 may be omitted. Further, the light-emitting device may be provided opposite the container 7 with the cloth W between, not in the container 7.

We claim:

1. A cloth inspecting device on a loom, which detects abnormality of a cloth (W) by detecting means (13) provided with a light-receiving device that moves in the width direction of said cloth (W) to receive light from said cloth (W) at a position alongside a cloth moving path in said loom, characterized in that said detecting means (13) is disposed in an elongated sealed container (7) having a window (8) formed of a transparent member, said detecting means being mounted for reciprocation in the lengthwise direction of said container (7), said container (7) being securely mounted at a position alongside said cloth moving path in such a way that said lengthwise direction of said container (7) is substantially parallel to said width direction of said cloth (W) and that said window (8) faces said cloth (W), said container extending across the width of said cloth with said detecting means (13) moveable within said container across the width of said cloth, means within said container for moving said detecting means, said window extending throughout the path of said detecting means, and said light-receiving device of said detecting means receives light from said cloth (W) through said window (8).

2. The cloth inspecting device according to claim 1, wherein said detecting means (13) includes a light-emitting device (19) for emitting light in a cloth inspecting area of the cloth, wherein said light-receiving device (23, 55, 56) receives reflected light from said cloth inspecting area, and wherein said light-receiving device (23, 55, 56) includes a filter (24, 35A, 35B).

3. The cloth inspecting device according to claim 2, wherein a plurality of said filters (35A, 35B) are provided, which filters constitute said light-receiving device (23, 55, 56) and which have a plurality of light-receiving elements (37a, 37b) with each filter having a different pattern of spacing between said light-receiving elements, and said detecting means (13) has selector means for selecting that filter from among those filters (35A, 35B) which is suitable from which to obtain cloth inspection information in association with a warp pitch of said cloth (W).

4. The cloth inspecting device according to claim 2, wherein said detecting means (13) is movably mounted on a rail (11) disposed in said container (7).

5. The cloth inspecting device according to claim 3, wherein said plurality of light receiving filters (35A, 35B) are provided on the same light-receiving device (23).

6. The cloth inspecting device according to claim 5, wherein a plurality of light-receiving devices are provided, and said light-receiving devices (55, 56) respectively receive incident light separated by an optical system for separating incident light from said cloth inspecting area into at least two parts.

7. The cloth inspecting device according to claim 3, wherein a plurality of light-receiving devices are provided, and said light-receiving devices (55, 56) respectively receive incident light separated by an optical system for separating incident light from said cloth inspecting area into at least two parts.

8. The cloth inspecting device according to claim 1 wherein said detecting means (13) is movably mounted on a rail (11) disposed in said container (7).

9. The cloth inspecting device according to claim 1, wherein said container (7) is arranged in contact with said cloth (W).

10. The cloth inspecting device according to claim 9, wherein said container (7) is arranged below a cloth passing position.

11. The cloth inspecting device according to claim 1, wherein said container (7) is so arranged as to face a reflector (9) with the cloth (W) therebetween.

12. The cloth inspecting device according to claim 11, wherein said reflector (9) is arranged so as to cover said window (8) of said container (7) at least over the area covered by said detecting means (13).

13. The cloth inspecting device according to claim 12, wherein said reflector (9) is arranged in contact with said cloth (W).

14. The cloth inspecting device according to claim 12, wherein said container (7) is arranged below a cloth passing position.

15. The cloth inspecting device according to claim 11, wherein said reflector (9) is arranged in contact with said cloth (W).

16. The cloth inspecting device according to claim 11, wherein said container (7) is arranged below a cloth passing position.

* * * * *